(12) United States Patent
Payne et al.

(10) Patent No.: US 8,210,177 B2
(45) Date of Patent: Jul. 3, 2012

(54) HUMIDIFICATION CHAMBERS

(75) Inventors: Simon Robert Payne, Dunsfold (GB);
Keethan Fernando, Bracknell (GB)

(73) Assignee: Intersurgical AG, Vaduz (LI)

( * ) Notice: Subject to any disclaimer, the term of this patent is extended or adjusted under 35 U.S.C. 154(b) by 680 days.

(21) Appl. No.: 12/376,913

(22) PCT Filed: Aug. 10, 2007

(86) PCT No.: PCT/GB2007/050486
§ 371 (c)(1),
(2), (4) Date: Feb. 9, 2009

(87) PCT Pub. No.: WO2008/017892
PCT Pub. Date: Feb. 14, 2008

(65) Prior Publication Data
US 2010/0170511 A1    Jul. 8, 2010

(30) Foreign Application Priority Data
Aug. 10, 2006    (GB) .................................. 0615871.1

(51) Int. Cl.
*A62B 9/00*    (2006.01)
(52) U.S. Cl. ......... 128/205.24; 128/203.15; 128/203.26; 251/12
(58) Field of Classification Search ........... 128/203.15–203.16, 203.26–203.27, 128/204.15–204.17, 205.24; 251/12
See application file for complete search history.

(56) References Cited

U.S. PATENT DOCUMENTS

| | | |
|---|---|---|
| 4,051,205 A | 9/1977 | Grant |
| 4,529,867 A | 7/1985 | Velnosky et al. |
| 4,913,140 A | 4/1990 | Orec et al. |
| 4,943,704 A | 7/1990 | Rabenau et al. |
| 5,195,515 A * | 3/1993 | Levine ..................... 128/203.26 |

(Continued)

FOREIGN PATENT DOCUMENTS

AU    468170    7/1973

(Continued)

OTHER PUBLICATIONS

International Preliminary Report on Patentability for International Application No. PCT/GB2007/050486 (Jan. 16, 2009).

(Continued)

*Primary Examiner* — Lynne Anderson
(74) *Attorney, Agent, or Firm* — LeClairRyan, a Professional Corporation

(57) ABSTRACT

A valve for controlling the level of liquid within a chamber (10) is disclosed. The valve comprises a liquid inlet (30) and a primary float (40) that is movable in response to a change in the level of liquid (20) within the chamber (10) between an open configuration in which liquid (20) is able to flow through the liquid inlet (30) into the chamber (10) when the liquid (20) within the chamber (10) is below a predetermined acceptable level, and a closed configuration in which liquid (20) is prevented from flowing through the liquid inlet (30) into the chamber (10) when the liquid within the chamber (10) is at or above the predetermined acceptable level. The valve also includes a secondary float (50) that is movable in response to an increase in the level of liquid within the chamber (10) above the predetermined acceptable level from an inoperative configuration to an operative configuration in which the secondary float (50) imparts a force upon the primary float (40) that urges the primary float (40) towards its closed configuration.

30 Claims, 5 Drawing Sheets

U.S. PATENT DOCUMENTS

| | | | |
|---|---|---|---|
| 5,426,271 A | 6/1995 | Clark et al. | |
| 5,445,143 A | 8/1995 | Sims | |
| 5,598,837 A | 2/1997 | Sirianne, Jr. et al. | |
| 5,782,258 A | 7/1998 | Herbon et al. | |
| 6,031,968 A | 2/2000 | Holtmann | |
| 6,981,514 B2 | 1/2006 | Nishi | |
| 7,047,999 B2 | 5/2006 | Payne | |
| 7,370,653 B2 | 5/2008 | Payne | |
| 7,383,852 B2 | 6/2008 | Pittaway et al. | |
| 7,735,486 B2 | 6/2010 | Payne | |
| 2002/0030005 A1 | 3/2002 | Crompton et al. | |
| 2004/0040599 A1* | 3/2004 | Payne | 137/409 |
| 2010/0171229 A1 | 7/2010 | Payne et al. | |

FOREIGN PATENT DOCUMENTS

| | | |
|---|---|---|
| DE | 298620 | 6/1917 |
| DE | 298620 A5 | 5/1992 |
| DE | 29617077 U1 | 1/1997 |
| EP | 0376584 A2 | 7/1990 |
| EP | 0589429 A1 | 3/1994 |
| EP | 2119466 A1 | 11/2009 |
| FR | 2602996 A1 | 2/1988 |
| GB | 1480786 | 7/1977 |
| GB | 2006023 A | 5/1979 |
| GB | 1589102 | 5/1981 |
| GB | 2209479 A | 5/1989 |
| JP | 2001349255 A | 12/2001 |
| JP | 3433397 B2 | 8/2003 |
| WO | 00/21602 A1 | 4/2000 |
| WO | 02/058770 A1 | 8/2002 |
| WO | 2005/011785 A1 | 2/2005 |
| WO | 2005/079898 A2 | 9/2005 |
| WO | 2008/017892 A1 | 2/2008 |
| WO | 2008/027670 A1 | 3/2008 |

OTHER PUBLICATIONS

International Search Report for International Patent Application No. PCT/GB2007/050486 (Jun. 12, 2007).

UK Search Report for UK International Patent Application No. GB0715526.0 (Nov. 22, 2007).

* cited by examiner

HUMIDIFICATION CHAMBERS

This invention relates to humidification chambers, and in particular to humidification chambers for use in a breathing circuit to humidify gases before inhalation.

The inhalation by patients of gases lacking sufficient moisture may damage or irritate the respiratory tract, and/or desiccate essential secretions, especially in the case of patients whose upper airways have been bypassed. Gases within a breathing circuit are therefore usually humidified before inhalation using a suitable humidification chamber.

Conventional humidification chambers generally contain a volume of water, and have two ports through which gases enter and exit the humidification chamber, and means for heating the water. Furthermore, many humidification chambers include means for replacing water that is lost from the humidification chamber so as to maintain the level of the water relatively constant. Such means typically takes the form of a liquid inlet valve having a float actuator, in which the rise and fall of the float actuator, in use, acts to open and close the valve so as to maintain the level of the water in the humidification chamber relatively constant.

Conventional liquid inlet valves may, however, become damaged so that the valve does not function correctly. In particular, small foreign objects may limit movement of the float actuator, and/or damage to the float actuator itself may reduce its buoyancy. In the event that the liquid inlet valve fails to close, the liquid level within the humidification chamber may continue to increase, during use, until water enters the breathing circuit of the patient. Water entering the breathing circuit is clearly potentially harmful to the patient, and hence humidification chambers have been developed that include a backup mechanism for preventing the inflow of water into the humidification chamber.

In particular, humidification chambers have been developed that include a secondary float actuator, which acts to close the liquid inlet valve in the event that the level of water in the humidification chamber becomes greater than that at which the primary float actuator closes the valve during normal operation. In this way, if the primary float actuator is not functioning correctly, for whatever reason, the secondary float actuator will act to close the liquid inlet valve before the level of water within the humidification chamber causes problems for the patient. However, such humidification chambers suffer from the disadvantage that their construction is often complex, and hence manufacturing costs may be significantly increased.

There has now been devised an improved valve and humidification chamber which overcome or substantially mitigate the above-mentioned and/or other disadvantages associated with the prior art.

According to a first aspect of the invention, there is provided a valve for controlling the level of liquid within a chamber, the valve comprising a liquid inlet and a primary float that is movable in response to a change in the level of liquid within the chamber between an open configuration in which liquid is able to flow through the liquid inlet into the chamber when the liquid within the chamber is below a predetermined acceptable level, and a closed configuration in which liquid is prevented from flowing through the liquid inlet into the chamber when the liquid within the chamber is at or above the predetermined acceptable level, wherein the valve includes a secondary float that is movable in response to an increase in the level of liquid within the chamber above the predetermined acceptable level from an inoperative configuration to an operative configuration in which the secondary float imparts a force upon the primary float that urges the primary float towards its closed configuration.

The valve of the present invention is particularly advantageous in relation to humidification chambers for use in a breathing circuit to humidify gases before inhalation. Hence, according to a further aspect of the invention, there is provided a humidification chamber for use in a breathing circuit to humidify gases before inhalation, the humidification chamber being adapted to contain a volume of liquid, and comprising a gas inlet port and a gas outlet port such that gases flow, in use, through the humidification chamber, and a valve as defined above for controlling the level of liquid within the humidification chamber.

The valve and humidification chamber according to the invention are advantageous principally because in the event that the primary float fails to move to its closed configuration when the liquid within the chamber is at or above the predetermined acceptable level, the increasing level of liquid within the chamber will cause the secondary float to impart a force upon the primary float that urges the primary float towards its closed configuration. Since the secondary float imparts a force upon the primary float, rather than being connected to a separate actuating member for closing the valve, the valve and humidification chamber of the present invention are of much simpler construction, and hence have significantly reduced manufacturing costs and are more reliable in operation, relative to prior art valves and humidification chambers.

The liquid is normally water, or a suitable aqueous solution. During use, the level of liquid within the humidification chamber will gradually reduce as the gases flowing through the chamber are humidified. Most preferably, the valve is adapted to maintain the level of liquid within the chamber within a relatively narrow range about the predetermined acceptable level.

The force imparted by the secondary float upon the primary float is preferably generated by the buoyancy of the secondary float, which will therefore increase as the level of liquid within the chamber increases. Said force preferably, therefore, increases until it is sufficient to overcome the cause of the primary float failing to move to its closed configuration. Probable causes of the primary float failing to move to its closed configuration include small foreign objects restricting movement of the primary float, and damage to the primary float reducing its buoyancy. The secondary float preferably has a greater buoyancy than the primary float. In particular, the secondary float preferably has a buoyancy that is at least twice as great, more preferably at least three times as great, and most preferably about four times as great, as the buoyancy of the primary float.

The primary float is preferably slidably mounted relative to the liquid inlet. In this case, the secondary float is preferably slidably mounted relative to the primary float. Most preferably, both the primary and secondary floats are slidably mounted relative to a guide sleeve. The guide sleeve preferably extends from an interior surface of the humidification chamber, and the liquid inlet is preferably disposed within the guide sleeve. In presently preferred embodiments, at least part of the primary float is slidably mounted within guide sleeve, and at least part of the secondary float is slidably mounted about the guide sleeve. In this case, the guide sleeve preferably includes longitudinal ribs on its interior surface that define channels along which liquid may flow down the exterior surface of the primary float.

The secondary float preferably engages the primary float directly in order to impart a force upon the primary float that urges the primary float towards its closed configuration. Preferably, this engagement is between cooperating formations on external surfaces of the primary and secondary floats. Most preferably, the secondary float includes at least one projection adapted to engage an operative surface of the primary float. The operative surface is preferably defined by the underside of at least one projection of the primary float. In presently preferred embodiments, the secondary float includes a central opening through which at least part of the primary float extends, and the central opening includes one or more projections adapted to engage one or more projections on an exterior surface of the primary float. In particular, the secondary float preferably includes an inwardly projecting, annular flange that engages one or more projections of the primary float. The flange is preferably provided with at least one opening, and preferably a series of openings, for enabling the passage of liquid through the flange during use.

The secondary float preferably comprises an air-filled internal chamber. This internal chamber is preferably provided with a vent, which is preferably formed in an upper wall of the secondary float, so as to prevent the build-up of excessive pressure within the secondary float during use.

The secondary float is preferably adapted to remain in its inoperative configuration during normal operation of the valve, when the level of liquid is close to the predetermined acceptable level. In particular, the float and/or chamber is preferably provided with means for maintaining the secondary float at or above a minimum height relative to the remainder of the humidification chamber, preferably such that the secondary float is spaced apart from the surface of the liquid during normal operation, thereby facilitating humidification of gases within the chamber. For instance, the secondary float may engage formations on an interior surface of the chamber, so as to maintain the secondary float at or above a minimum height relative to the remainder of the humidification chamber. Alternatively, the secondary float may include one or more legs adapted to rest upon a lower interior surface of the humidification chamber, so as to maintain the secondary float at or above a minimum height relative to the remainder of the humidification chamber. In this case, preferably only a lower portion of the legs of the secondary float are submerged during normal operation of the valve, such that the remainder of the secondary float is spaced apart from the surface of the liquid.

The secondary float is preferably formed of injection moulded plastics material. Preferably, the secondary float comprises a plurality of members, and most preferably two members, that are engageable with one another so that they together define the internal chamber of the secondary float. In presently preferred embodiments, the engageable members include cooperating formations that fix the members together, most preferably with a snap fit. The engageable members may also be glued together. Said cooperating formations may conveniently be deformable projections with enlarged heads, which engage each other with a snap fit. In presently preferred embodiments, the secondary float comprises two engageable members that are injection moulded as a single component, in which the two members are joined by a hinge and are rotatable into engagement with each other.

The valve preferably includes a valve seat, and either the primary float or a separate actuating member is preferably engageable with the valve seat so as to control flow of liquid through the liquid inlet into the chamber. In the open configuration, the primary float or the actuating member is preferably disengaged from the valve seat and liquid is able to flow through the liquid inlet into the chamber, and in the closed configuration the primary float or the actuating member is preferably engaged with the valve seat and liquid is prevented from flowing through the liquid inlet into the chamber. Where a separate actuating member is engageable with the valve seat, the actuating member is preferably operably linked to the primary float so as to be movable in response to movement of the primary float. In presently preferred embodiments, the actuating member has the form of a valve cushion that is engaged with the primary float. The actuating member and/or the valve seat is preferably formed of a resilient material, such as a thermoplastic elastomer, in order to form a reliable and effective seal.

The liquid inlet of the valve preferably has the form of a liquid conduit extending through a wall of the humidification chamber. The liquid inlet is preferably adapted at one end for connection to a source of liquid, and at the other end for introducing liquid into the chamber. Most preferably, the liquid inlet includes an opening through which liquid may enter the chamber, and the valve seat preferably extends about this opening. The opening is preferably of reduced diameter relative to the remainder of the liquid inlet, and the liquid inlet preferably includes a tapered end portion that leads to the opening. The valve seat is preferably formed integrally with the liquid inlet, and preferably has a narrow operative surface.

The humidification chamber preferably comprises an upper portion that is formed of plastic material, most preferably by injection moulding, and a base formed of a good heat conductor, such as a suitable metal, that together define an enclosure for containing the liquid. The base is preferably generally circular in shape, and the upper portion preferably has a generally cylindrical side wall. The gas inlet port and gas outlet port are preferably formed in an upper wall of the humidification chamber, and preferably comprise upstanding tubular connectors that are adapted for connection to conventional respiratory connectors and tubing. The liquid inlet and the guide sleeve are preferably formed integrally with the upper portion of the humidification chamber, and are preferably situated generally centrally in an upper wall of the humidification chamber.

Preferred embodiments of the invention will now be described in greater detail, by way of illustration only, with reference to the accompanying drawings, in which FIG. 1 is a first cross-sectional view of a humidification chamber according to the invention, in which a primary float is acting to maintain a liquid inlet valve in a closed configuration;

Figure 1:
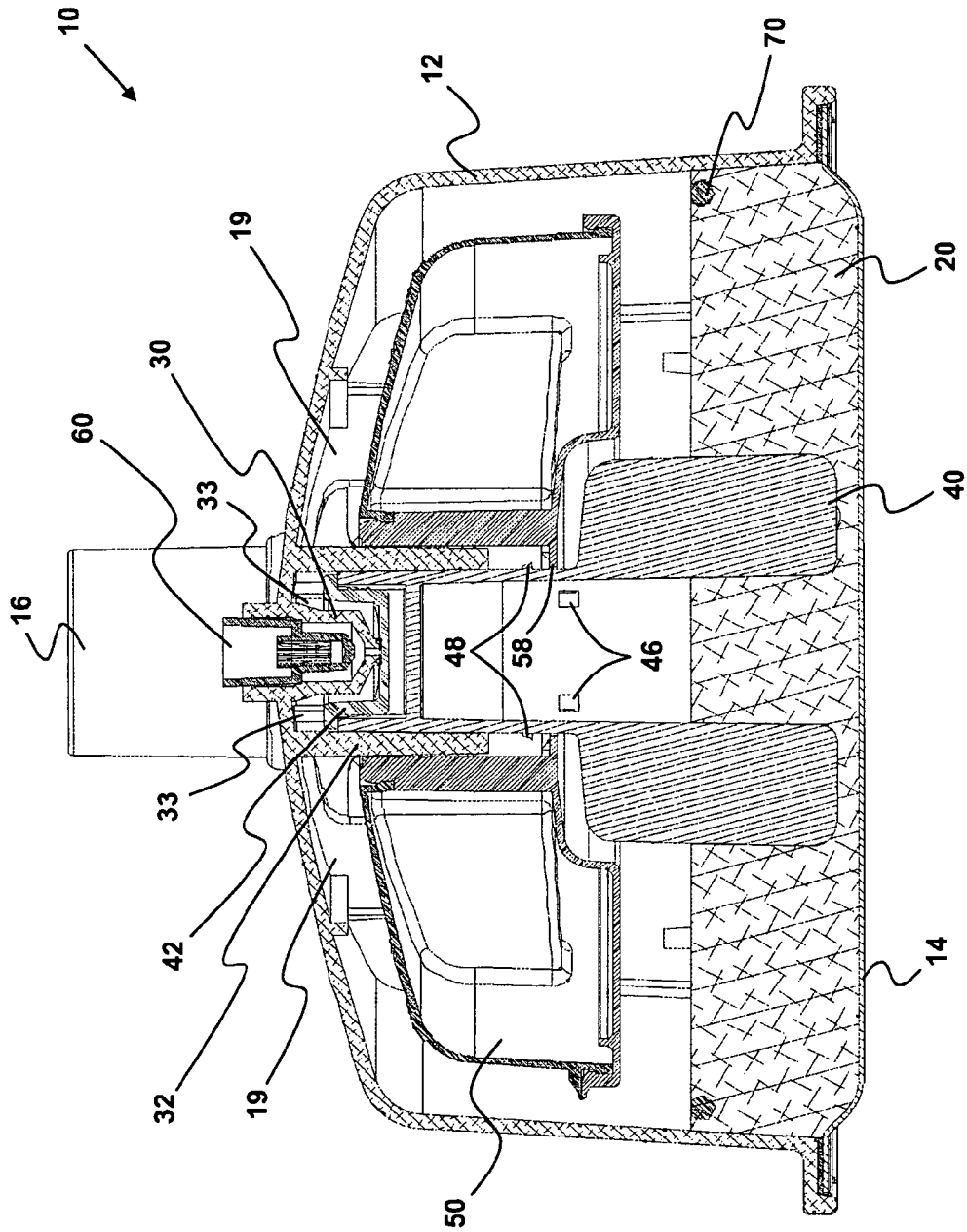
Figure 2:
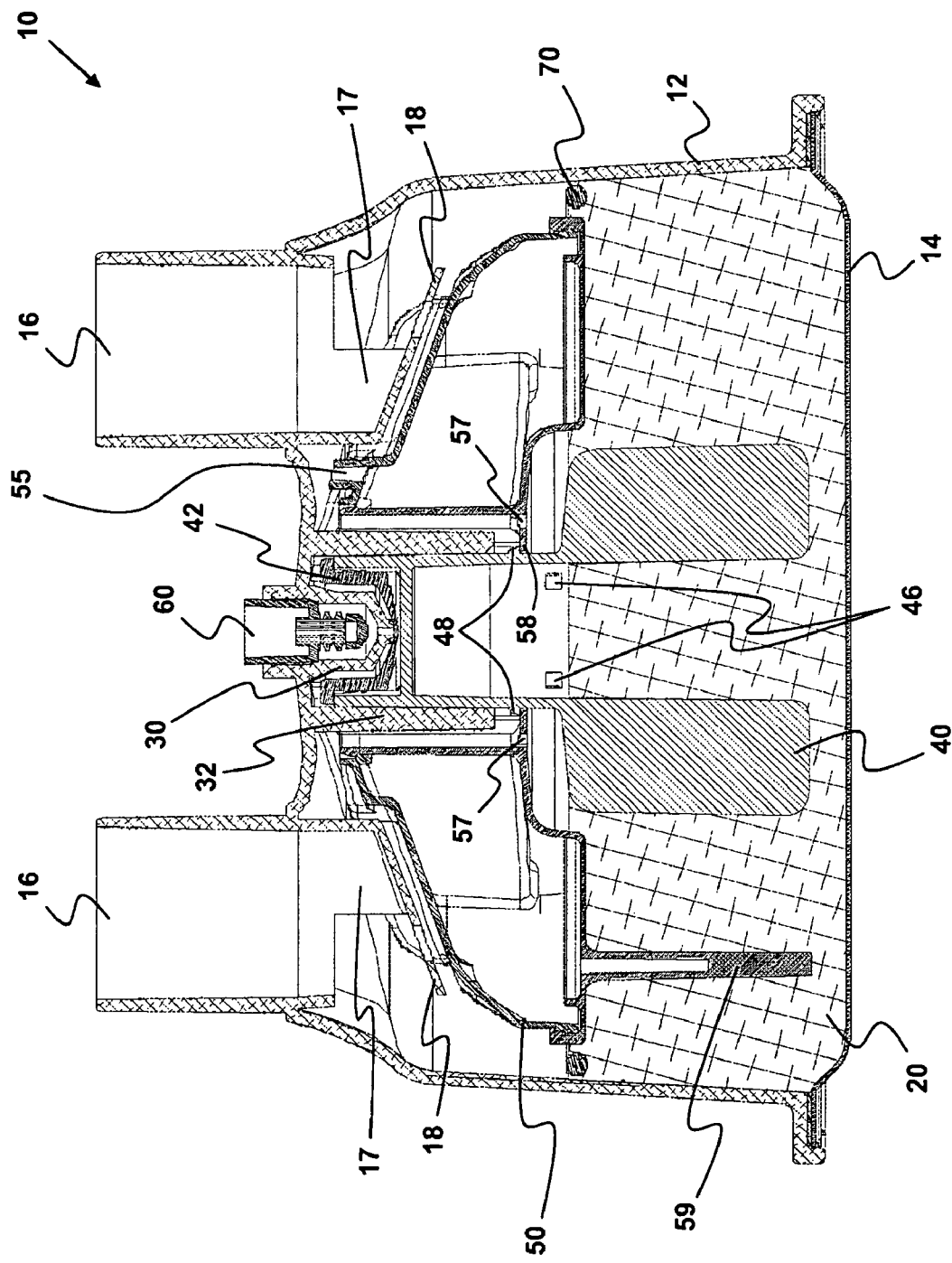
FIG. 2 is a second cross-sectional view of the humidification chamber, in which a secondary float is acting to maintain a liquid inlet valve in a closed configuration.

FIGS. 1 and 2 show a humidification chamber according to the invention, which is generally designated 10. The humidification chamber 10 comprises a body 12 that is injection moulded in a transparent plastics material, and a metal base 14 fixed to an open lower end of the body 12. The body 12 and the base 14 of the humidification chamber 10 cooperate to define an enclosure for containing, in use, a volume of water 20.

The body 12 of the humidification chamber 10 comprises a generally cylindrical, but slightly tapered, side wall that is fixed at its lower end to the periphery of the base 14, and an upper wall that has the general shape of a shallow dome. The base 14 of the humidification chamber 10 has the form of a circular disc, with an upturned rim that is sealed to a flange at the lower end of the side wall of the body 12.

Two inlet/outlet ports 16 that have the form of 22 mm tubular connectors extend upwardly from openings in the upper wall of the humidification chamber 10. Each inlet/outlet port 16 also includes a hemi-cylindrical extension 17 and a circular end baffle 18 within the enclosure of the humidification chamber 10, which together define a lower opening that faces the side wall of the humidification chamber 10. In addition, the humidification chamber 10 includes four baffles 19 (two of which are visible in FIG. 1) that are each formed integrally with the body 12 of the humidification chamber 10, and each extend downwardly from the interior surface of the upper wall. Each baffle 19 is arcuate in its horizontal dimension, and extends horizontally between an interior surface of the side wall of the humidification chamber 10 and a position adjacent to, but separated from, the guide sleeve 32.

Figure 5:
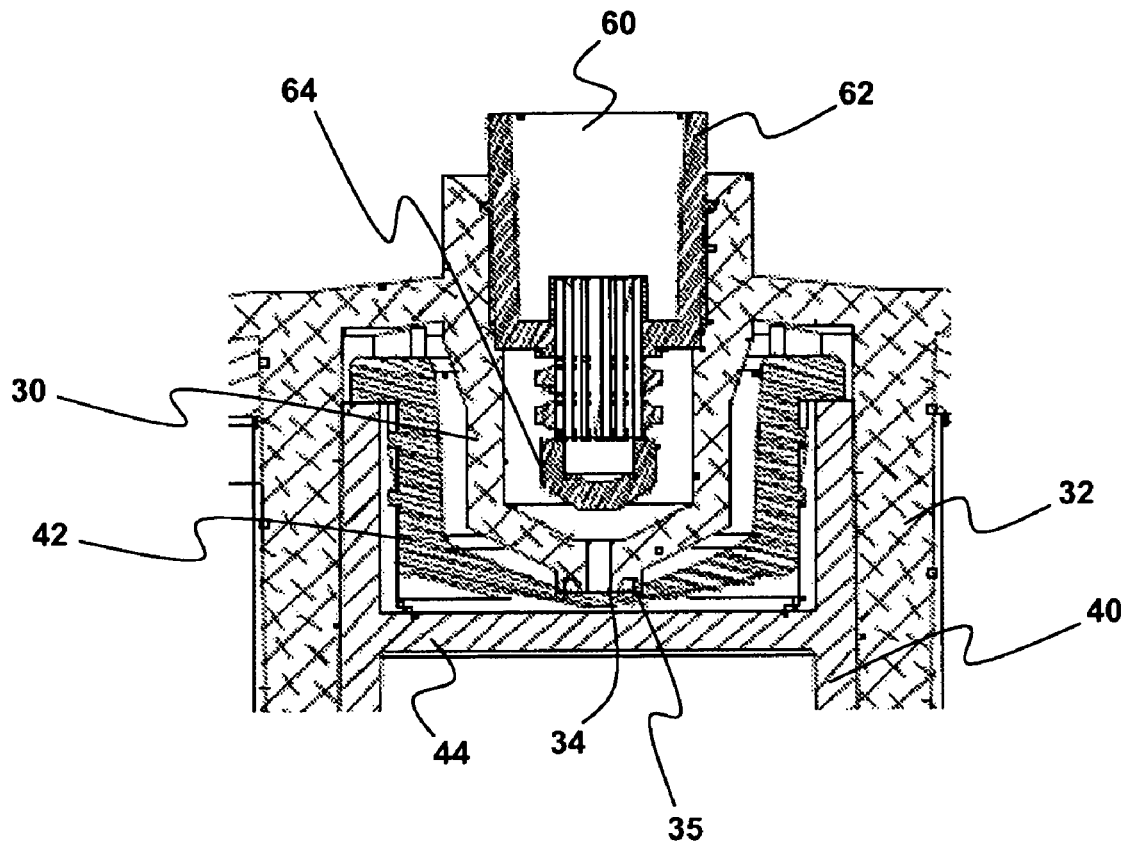
FIG. 5 is a fragmentary cross-sectional view of a liquid inlet valve of the humidification chamber.

Referring now also to FIG. 5, the humidification chamber 10 also comprises a liquid inlet 30 that extends through an opening in the centre of the upper wall of the humidification chamber 10. The liquid inlet 30 comprises an upper cylindrical portion with an open upper end, an intermediate cylindrical portion of reduced diameter, and a tapered lower end portion that terminates within the humidification chamber 10 with a lower opening of significantly reduced diameter relative to the open upper end.

As shown most clearly in FIG. 5, the exterior surface of the liquid inlet 30 that surrounds the lower opening comprises two concentric projections, the inner projection being of greater extent than the outer projection. These concentric projections each terminate with a relatively narrow edge, and these relatively narrow edges define an inner valve seat 34 and an outer valve seat 35, which are both adapted to form a seal with an elastomeric valve cushion 42 that is described in more detail below.

Figure 6:
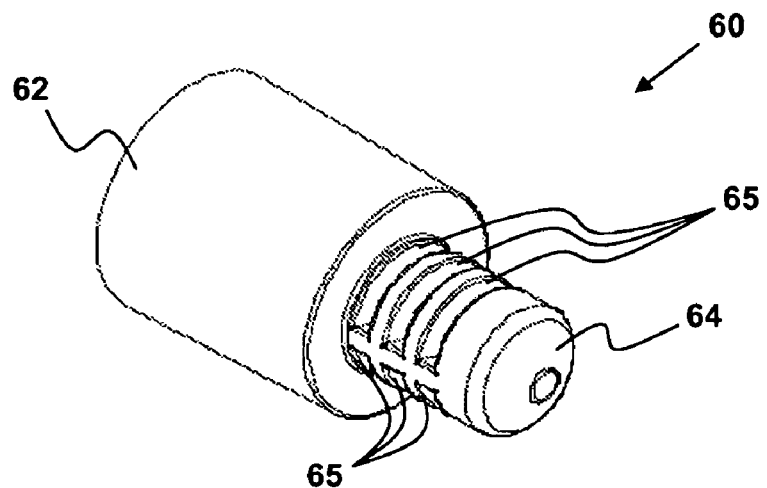
FIG. 6 is a perspective view of a liquid inlet filter of the humidification chamber.
Figure 7:
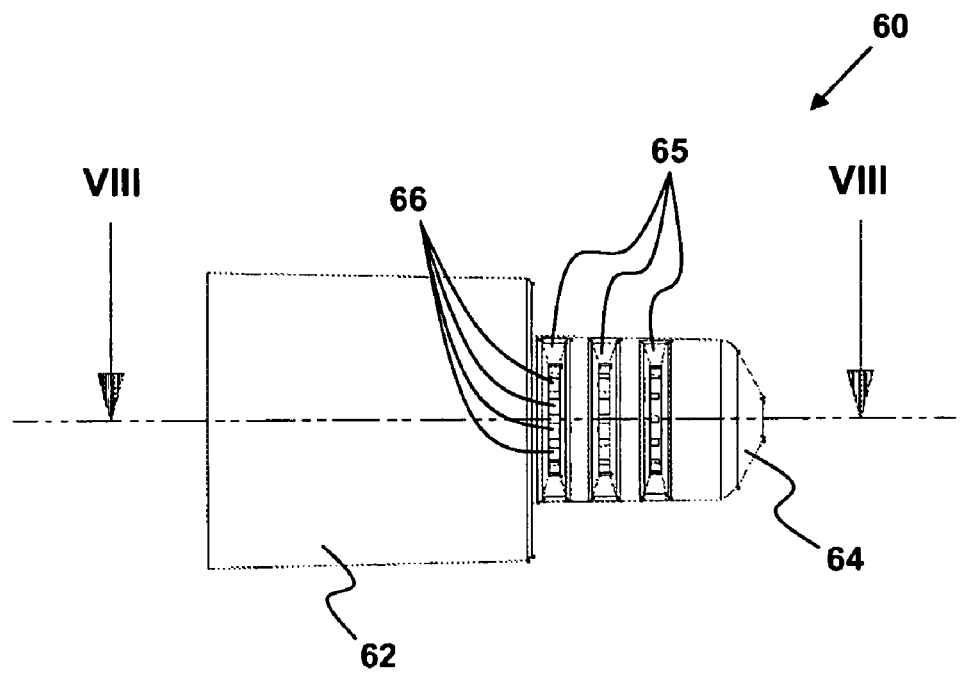
FIG. 7 is a side view of the liquid inlet filter.
Figure 8:
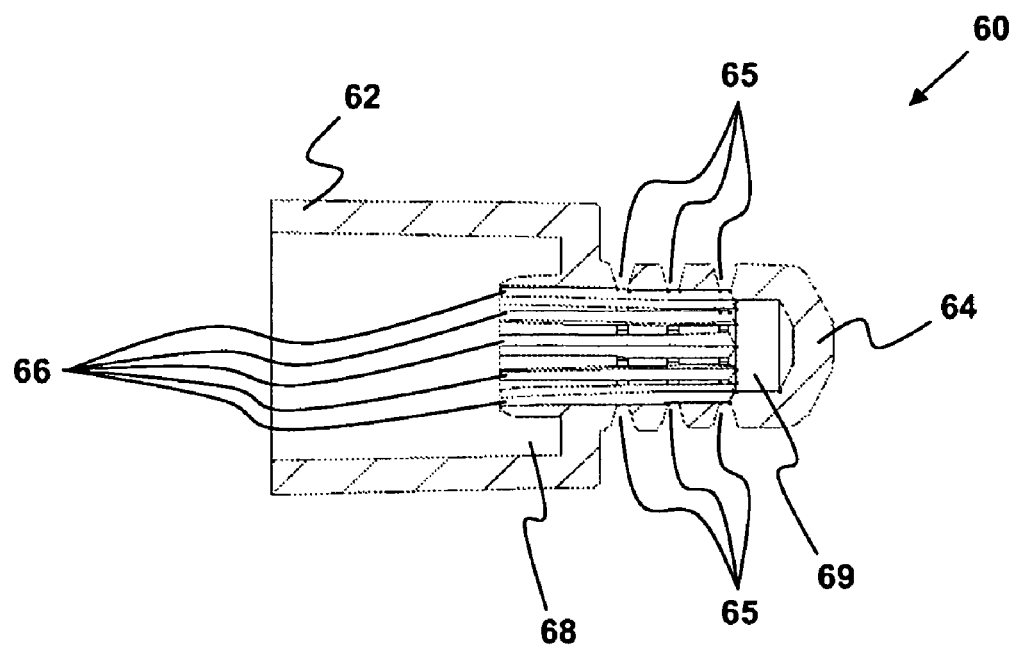
FIG. 8 is a cross-sectional view, along the line VIII-VIII in FIG. 7, of the liquid inlet filter.

A filter 60 is fixed within the liquid inlet 30 so that water flowing through the liquid inlet 30 necessarily flows through the filter 60. The filter 60 is shown most clearly in FIGS. 6, 7 and 8, and comprises a cylindrical inlet portion 62, and a cylindrical outlet portion 64 of reduced diameter. The inlet portion 62 has an open end, and an end from which the outlet portion 64 projects. The outlet portion 64 has an open end situated a short distance within the inlet portion 62, so as to define an annular, first collection chamber 68 of the filter 60, and the outlet portion 64 extends through the end wall of the inlet portion 62. The projecting part of the outlet portion 64 has a closed end and a side wall that includes six elongate openings 65, which each reduce gradually in width before leading into the interior of the outlet portion 64. The openings 65 are arranged in three circumferentially-extending pairs at equally spaced positions along the longitudinal axis of the outlet portion 64. Furthermore, longitudinal members 66 that extend perpendicularly across the openings 65 are formed on the interior surface of the outlet portion 64, so that an array of apertures is defined in the side wall of the outlet portion 64. An end portion of the outlet portion 64 does not include any apertures, and hence defines a second collection chamber 69 of the filter 60. In this embodiment, the filter 60 is injection moulded in polycarbonate plastics material, and each aperture has a width of approximately 0.26 mm and a length of approximately 0.36 mm.

The inlet portion 62 of the filter 60 is received with an interference fit within the upper portion of the liquid inlet 30, and is fixed using suitable adhesive so that there is a seal between the external surface of the inlet portion 62 of the filter 60 and the interior surface of the upper portion of the liquid inlet 30. The outlet portion 64 of the filter 60 is sized so that its exterior surface is separated, at all points, from the interior surface of the intermediate portion and tapered lower end portion of the liquid inlet 30. The inlet portion 62 of the filter 60 is also appropriately sized so as to receive a connector of a suitable liquid conduit, such that the liquid inlet 30 communicates with a source of water during use.

As shown in FIGS. 1 and 2, the upper wall of the humidification chamber 10 includes a centrally positioned and downwardly extending guide sleeve 32 of cylindrical shape, which is of greater diameter than the liquid inlet 30 and extends co-axially therewith. Eight longitudinal ribs 33 are provided on the interior surface of the guide sleeve 32 at equiangularly spaced positions, so as to form channels for the water 20 being supplied through the liquid inlet 30 to flow down the exterior surface of the primary float 40 during use.

Figure 3:
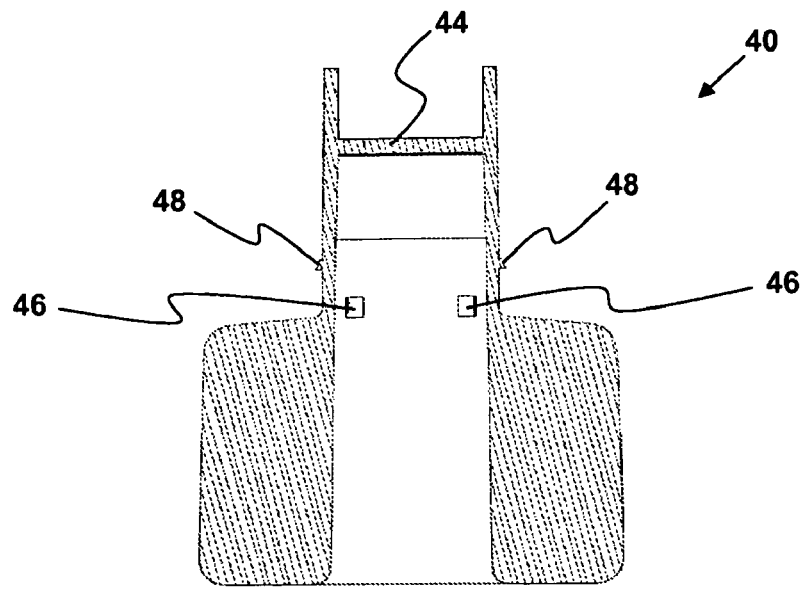
FIG. 3 is a cross-sectional view of the primary float.

A liquid inlet valve controls the flow of water 20 through the liquid inlet 30. The liquid inlet valve comprises a primary float 40, a valve cushion 42, and a secondary float 50. The primary float 40 is shown in isolation in FIG. 3, and comprises an upper portion and a lower portion, which are integrally formed in a plastics material using an injection moulding process that is described in published European patent application EP 1366881.

The upper portion of the primary float 40 is a generally cylindrical tube with relatively thin walls and a diameter that increases gradually and slightly from an open upper end to a open lower end. The exterior surface of the upper portion is highly polished to enable a low-friction slidable engagement with the guide sleeve 32, and includes a pair of circumferentially extending, and diametrically opposed, projections 48. These projections 48 are adapted to be engaged by the secondary float 50, as discussed in more detail below, and each comprises an operative lower surface that is orientated perpendicularly to the adjacent surface of the upper portion of the primary float 40.

A circular partition 44 extends across the interior of the upper portion of the primary float 40 so as to define a cylindrical recess in the upper surface of the primary float 40. In addition, the upper portion includes four openings 46, at equiangularly spaced positions, in a lower part of its wall below the circular partition 44.

The lower portion of the primary float 40 is also generally cylindrical in form, but has walls of greater thickness than those of the upper portion of the float 40. The plastics material of the lower portion has a foam-like structure with many pockets of gas trapped within the plastics material. The primary float 40 is located within the enclosure of the humidification chamber 10 such that the lower end of the primary float 40 rests on the base 14 of the humidification chamber 10 until a sufficient volume of water 20 is introduced into the humidification chamber 10, and the majority of the upper portion of the primary float 40 is received with a slidable fit within the guiding sleeve 46.

A valve cushion 42, which is formed of elastomeric material, has the form of a cup and is received with an interference fit within the cylindrical recess in the upper surface of the primary float 40. The open upper end of the valve cushion 42 has an outwardly extending flange that rests upon the rim of the upper portion of the primary float 40, and the base of the valve cushion 42 is separated from the circular partition 44 of the primary float 40 so as to allow deformation of the valve cushion 42 towards the central partition 44 during use.

Figure 4:
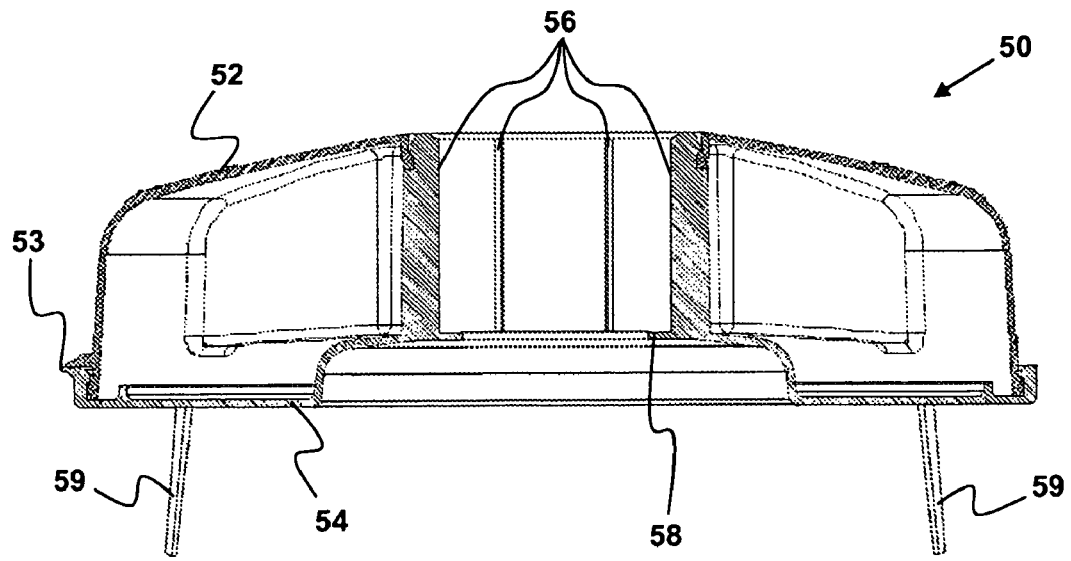
FIG. 4 is a cross-sectional view of the secondary float.

The secondary float 50 is shown in isolation in FIG. 4, and comprises upper and lower members 52,54 that are injection moulded as a single component, and joined by a hinge 53. The upper and lower members 52,54 together define an internal chamber that provides the secondary float 50 with approximately four times the buoyancy of the primary float 40. However, as shown in FIG. 2, a vent 55 is provided in the upper wall of the secondary float 50 to prevent the build-up of excessive pressure within the secondary float 50 during use.

The upper member 52 defines a side wall and an upper wall of the secondary float 50, and the lower member 54 defines an cylindrical inner wall and a base of the secondary float 50. The inner edge of the upper member 52, and the upper edge of the lower member 54, are formed with corresponding annular projections with enlarged heads that engage each other with a snap fit. Similarly, the outer edges of the upper and lower members 52,54 are formed with corresponding annular projections with enlarged heads that engage each other with a snap fit. In this way, the upper and lower members 52,54, joined by the hinge 53, are injection moulded as a single component, and the upper and lower members 52,54 are then rotated into engagement with each other, with a snap fit, so as to form the secondary float 50. The snap fit between corresponding projections is adapted to prevent the ingress of water into the internal chamber of the secondary float 50 during use. If necessary, however, the upper and lower members 52,54 are also glued together.

The upper member 52 of the secondary float 50 has a shape that conforms generally to the interior surface of the upper wall of the humidification chamber 10, such that the secondary float 50 is adapted to lie alongside the upper wall of the humidification chamber 10. In particular, the upper member 52 has a generally cylindrical, but slightly tapered, side wall and an annular upper wall, as shown most clearly in FIGS. 1 and 4. In addition, the upper member 52 comprises shallow depressions for accommodating the extensions 17 and baffles 18 of the inlet/outlet ports 16, as shown most clearly in FIG. 2, and more extensive recesses for accommodating the arcuate baffles 19 extending from the upper wall of the humidification chamber 10.

The lower member 54 comprises an annular base that is shaped so as to accommodate an upper part of the lower portion of the primary float 40, and a cylindrical inner portion that is adapted for slidable engagement with the exterior surface of the guide sleeve 32. The cylindrical inner portion has open upper and lower ends, and six longitudinal ribs 56 formed on its inner surface at equiangularly spaced positions. In addition, an annular flange 58 extends inwardly from the lower end of the inner portion of the secondary float 50, and includes an operative upper surface adapted to engage the projections 48 on the exterior surface of the primary float 40. The flange 58 also includes a series of openings 57 for enabling the throughflow of water 20 during use.

The lower member 54 also includes three legs 59 that rest upon the base 14 of the humidification chamber 10, and hence maintain the secondary float 50 at a minimum height, during normal operation. As shown in FIG. 2, the legs 59 each include an internal chamber that is in communication with the remainder of the interior of the secondary float 50.

Finally, the humidification chamber 10 includes a liquid level indicator 70 that enables a user to readily ascertain the level of the water 20. This liquid level indicator comprises an annular float 70 and suitable level indication marks (not visible in FIGS. 1 and 2), and is described in published European patent application EP 1347797.

The humidification chamber 10 is connected to a breathing circuit by attaching a gas inlet conduit (not shown in the Figures) to one of the inlet/outlet ports 16, and attaching a gas outlet conduit to the other inlet/outlet port 16. A heat source (not shown in the Figures) is placed in contact with the base 14 of the humidification chamber 10, so as to heat the water 20 within the humidification chamber 10 to a desired temperature.

A liquid conduit (not shown in the Figures) is then connected at one end to a source of water, and at the other end to the liquid inlet 30, so that water 20 is continuously supplied to the filter 60 and liquid inlet 30. When the source of water 20 is first connected to the humidification chamber 10, water 20 flows through the filter 60 and liquid inlet 30, fills the valve cushion 42, and then flows through the channels defined by the longitudinal ribs 33 of the guiding sleeve 32, through the openings 57 in the flange 58 of the secondary float 50, and down the exterior surface of the primary float 40 onto the base 14 of the humidification chamber 10. The humidification chamber 10 therefore begins to fill with water 20.

The source of water may be a container, such as a flexible bag, that is charged with water, or some other kind of water reservoir. Such sources often contain foreign objects, which may be present as a result of the manufacture, storage and/or previous use of the bag or reservoir. However, the filter 60 acts to prevent the passage of foreign objects through the liquid inlet 30 into the enclosure of the humidification chamber 10. In use, foreign objects collect, under the influence of gravity, in either the first collection chamber 68 in the inlet portion 62 of the filter 60, or the second collection chamber 69 in the outlet portion 64 of the filter 60. In each case, the collected foreign objects within the first and second collection chambers 68,69 are far removed from the open upper end of the outlet portion 64 and the apertures in the side wall of the outlet portion 64, and hence will not impede the flow of water through the filter 60 or interfere with normal operation of the valve mechanism.

When the water 20 within the humidification chamber 10 reaches a certain level, the primary float 40 is raised relative to the remainder of the humidification chamber 10 by its buoyancy. The primary float 40 is held in an upright position by the guiding sleeve 32. The primary float 40 will continue to rise until the water 20 reaches a sufficient level for the valve cushion 42 to be urged against the inner valve seat 34 of the liquid inlet 30 with enough force to form an effective seal, and hence prevent the inflow of water 20 through the lower opening of the liquid inlet 30. This configuration is shown in FIG. 1.

There will generally be some deformation of the valve cushion 42 towards the central partition 44 of the primary float 40 before an effective seal is formed between the valve cushion 42 and the inner valve seat 34, so that the inflow of water 20 into the humidification chamber 10 ceases. In the event that an effective seal is not formed between the valve cushion 42 and the inner valve seat 34, for instance due to the presence of foreign bodies on the operative surfaces of the valve cushion 42 and/or the inner valve seat 34, the primary float 40 will continue to rise and deformation of the valve cushion 42 will increase until the valve cushion 42 is urged against the outer valve seat 35 of the liquid inlet 30 with enough force to form an effective seal, and hence prevent the inflow of water 20 through the lower opening of the liquid inlet 30.

In use, gases intended for inhalation by a patient are supplied to the gas inlet conduit under positive pressure. The pressure differential created between the gas inlet conduit and the gas outlet conduit causes gases to flow from the gas inlet conduit, through the enclosure of the humidification chamber 10, to the gas outlet conduit. This causes water vapour within the chamber 10 to be entrained in the flow of gas through the humidification chamber 10, so that the gas within the gas outlet conduit has an increased humidity relative to the gas within the gas inlet conduit.

As water is entrained in the flow of gas through the humidification chamber 10, the level of the water 20 in the humidification chamber 10 will gradually reduce. The primary float 40 will therefore be lowered relative to the remainder of the humidification chamber 10. This will continue until the valve cushion 42 of the liquid inlet valve becomes separated from the lower opening of the liquid inlet 30, such that water 20 is allowed to flow into the humidification chamber 10 through the liquid inlet 30. As the level of water 20 increases once again, the primary float 40 will rise relative to the remainder of the humidification chamber 10. The primary float 40 will continue to rise until the water 20 reaches a sufficient level for the valve cushion 42 to be once again urged against the inner and/or outer valve seat 34,35 of the lower opening of the liquid inlet 30 with enough force to form an effective seal, and hence prevent the inflow of water 20 through the lower opening. In this way, the level of the water 20 is maintained relatively constant during use. In addition, the openings in the primary float 40 prevent the buoyancy of the primary float 40 being affected by air becoming trapped between the surface of the water 20 and the interior surface of the lower portion of the primary float 40.

In the event that the liquid inlet valve becomes damaged, for instance by small foreign objects limiting movement of the primary float 40 and/or damage to the primary float 40 reducing its buoyancy, the level of water 20 within the humidification chamber 10 will rise beyond the level at which the liquid inlet valve closes during normal operation. However, when the water 20 within the humidification chamber 10 reaches a certain level, the secondary float 50 is raised relative to the remainder of the humidification chamber 10 by its buoyancy, and held in an upright position by the guiding sleeve 32.

The secondary float 50 will continue to rise until the water 20 reaches a sufficient level for the flange 58 of the secondary float 50 to impinge upon, and hence engage, the projections 48 of the primary float 40. As the level of water 20 within the humidification chamber 10 increases, the upward buoyancy force imparted upon the secondary float 50, and hence the upward force imparted by the secondary float 50 upon the primary float 40, will increase until the primary float 40 is raised relative to the remainder of the humidification chamber 10. Since the secondary float 50 has a buoyancy that is approximately four times the buoyancy of the primary float 40, the upward force imparted by the secondary float 50 upon the primary float 40 will overcome common damage to the liquid inlet valve, such as limitation in the movement of the primary float 40 and/or damage to the primary float 40 reducing its buoyancy. The upward force imparted by the secondary float 50 upon the primary float 40 will cause the primary float 40 to be raised relative to the remainder of the humidification chamber 10 until the valve cushion 42 is urged against the inner valve seat 34 and/or the outer valve seat 35 of the liquid inlet 30 with enough force to form an effective seal, and hence prevent the inflow of water 20 through the lower opening of the liquid inlet 30, as discussed in detail above. This configuration is shown in FIG. 2.

The invention claimed is:

1. A valve for controlling the level of liquid within a chamber, the valve comprising a liquid inlet and a primary float that is movable in response to a change in the level of liquid within the chamber between an open configuration in which liquid is able to flow through the liquid inlet into the chamber when the liquid within the chamber is below a predetermined acceptable level, and a closed configuration in which liquid is prevented from flowing through the liquid inlet into the chamber when the liquid within the chamber is at or above the predetermined acceptable level, wherein the valve includes a secondary float that is movable in response to an event when the primary float fails to move to its closed configuration resulting in an increase in the level of liquid within the chamber above the predetermined acceptable level from an inoperative configuration to an operative configuration in which the secondary float engages the primary float directly to impart a force upon the primary float that urges the primary float towards its closed configuration.

2. A valve as claimed in claim 1, wherein the valve is adapted to maintain the level of liquid within the chamber within a relatively narrow range about the predetermined acceptable level.

3. A valve as claimed in claim 1, wherein the force imparted by the secondary float upon the primary float is generated by the buoyancy of the secondary float.

4. A valve as claimed in claim 3, wherein the secondary float has a greater buoyancy than the primary float.

5. A valve as claimed in claim 4, wherein the secondary float has a buoyancy that is at least twice as great as the buoyancy of the primary float.

6. A valve as claimed in claim 5, wherein the secondary float has a buoyancy that is at least three times as great as the buoyancy of the primary float.

7. A valve as claimed in claim 1, wherein the primary float is slidably mounted relative to the liquid inlet.

8. A valve as claimed in claim 7, wherein the secondary float is slidably mounted relative to the primary float.

9. A valve as claimed in claim 1, wherein the primary and secondary floats are slidably mounted relative to a guide sleeve.

10. A valve as claimed in claim 9, wherein the guide sleeve extends from an interior surface of the chamber, and the liquid inlet is disposed within the guide sleeve.

11. A valve as claimed in claim 10, wherein at least part of the primary float is slidably mounted within the guide sleeve, and at least part of the secondary float is slidably mounted about the guide sleeve.

12. A valve as claimed in claim 11, wherein the guide sleeve includes longitudinal ribs on its interior surface that define channels along which liquid may flow down the exterior surface of the primary float.

13. A valve as claimed in claim 1, wherein the engagement between the primary float and the secondary float is between cooperating formations on external surfaces of the primary and secondary floats.

14. A valve as claimed in claim 13, wherein the secondary float includes at least one projection adapted to engage an operative surface of the primary float.

15. A valve as claimed in claim 14, wherein the operative surface is defined by the underside of at least one projection of the primary float.

16. A valve as claimed in claim 13, wherein the secondary float includes a central opening through which at least part of the primary float extends, and the central opening includes one or more projections adapted to engage one or more projections on an exterior surface of the primary float.

17. A valve as claimed in claim 16, wherein the secondary float includes an inwardly projecting, annular flange that engages one or more projections of the primary float.

18. A valve as claimed in claim 17, wherein the flange is provided with at least one opening for enabling the passage of liquid through the flange during use.

19. A valve as claimed in claim 1, wherein the secondary float comprises an air-filled internal chamber, and the internal chamber is provided with a vent so as to prevent the build-up of excessive pressure within the secondary float during use.

20. A valve as claimed in claim 1, wherein the secondary float is adapted to remain in its inoperative configuration during normal operation of the valve, when the level of liquid is close to the predetermined acceptable level.

21. A valve as claimed in claim 20, wherein the secondary float and/or the chamber is provided with formations for maintaining the secondary float at or above a minimum height relative to the remainder of the humidification chamber, during normal operation of the valve.

22. A valve as claimed in claim 21, wherein the secondary float is spaced apart from the surface of the liquid during normal operation.

23. A valve as claimed in claim 20, wherein the secondary float engages formations on an interior surface of the chamber, so as to maintain the secondary float at or above a minimum height relative to the remainder of the humidification chamber.

24. A valve as claimed in claim 20, wherein the secondary float includes one or more legs adapted to rest upon a lower interior surface of the chamber, so as to maintain the internal chamber of the secondary float at or above a minimum height relative to the remainder of the chamber.

25. A valve as claimed in claim 24, wherein only a lower portion of the one or more legs of the secondary float is submerged during normal operation of the valve, such that the remainder of the secondary float is spaced apart from the surface of the liquid.

26. A valve as claimed in claim 1, wherein the secondary float comprises a plurality of members that are engageable with one another so that they together define the internal chamber of the secondary float.

27. A valve as claimed in claim 26, wherein the engageable members of the secondary float include cooperating formations that fix the members together.

28. A valve as claimed in claim 26, wherein the secondary float comprises two engageable members that are injection moulded as a single component, in which the two members are joined by a hinge and are rotatable into engagement with each other.

29. A valve as claimed in claim 1, wherein the valve is adapted for incorporation into a humidification chamber for use in a breathing circuit to humidify gases before inhalation.

30. A humidification chamber for use in a breathing circuit to humidify gases before inhalation, the humidification chamber being adapted to contain a volume of liquid, and comprising a gas inlet port and a gas outlet port such that gases flow, in use, through the humidification chamber, and a valve as claimed in claim 1 for controlling the level of liquid within the humidification chamber.

* * * * *